United States Patent [19]

Mohammed

[11] 4,014,691

[45] Mar. 29, 1977

[54] DENTAL BRIDGE ALLOY

[76] Inventor: M. Hamdi A. Mohammed, 50 Ranger Lane, West Hartford, Conn. 06117

[22] Filed: Mar. 22, 1974

[21] Appl. No.: 453,845

Related U.S. Application Data

[63] Continuation-in-part of Ser. No. 316,272, Dec. 18, 1972, abandoned.

[52] U.S. Cl. .................... 75/171; 75/134 F; 148/32

[51] Int. Cl.[2] .................... C22C 19/00

[58] Field of Search .................... 75/171, 170, 134 F; 148/32, 32.5

[56] References Cited

UNITED STATES PATENTS

| | | | |
|---|---|---|---|
| 1,958,446 | 5/1934 | Prange | 75/171 |
| 3,366,478 | 1/1968 | Wheaton | 75/171 |
| 3,723,107 | 3/1973 | Richards et al. | 75/171 |
| 3,790,372 | 2/1974 | Chaturvedi | 75/171 |

*Primary Examiner*—R. Dean
*Attorney, Agent, or Firm*—Prutzman, Hayes, Kalb & Chilton

[57] ABSTRACT

A highly ductile cobalt-chromium-nickel dental alloy suited for crown and bridge applications which require deformation by hand burnishing in the mouth of a patient, has a controlled high stacking fault energy and a ductility of about 20 percent elongation or more, a yield strength of about 35,000 psi or less and low work hardening characteristics and is free of hardening precipitates resulting from the inclusion of significant amounts of carbon, boron, molybdenum, titanium, aluminum, and tungsten in the alloy. Preferably, the nickel-cobalt ratio in the alloy base ranges from a low of about 1:3, by weight, to prevent the normal transformation of cobalt from a ductile face centered cubic lattice to a hexagonal close pack structure upon cooling to room temperature to a high of 2:1 since higher concentrations of nickel produce $CoNi_3$. The alloy base preferably includes 20 percent chromium to provide the necessary corrosion resistance and an additional amount of 2 percent nickel is required in the alloy base to offset the adverse effects of chromium on the ductility of the alloy. A small quantity of niobium or tantalum, both of which have substantial solubility in the alloy base, are added to form nuclei of crystallization for the alloy to promote fineness of crystal size and uniformity of physical properties from melt-to-melt. Niobium and tantalum also counteract the adverse effect of chromium on the stacking fault energy of the alloy with 1 percent of niobium, or approximately 2 percent of tantalum, counteracting the adverse effect of 1.25 percent chromium so that the nickel used in the alloy base can be reduced according to the amount of niobium or tantalum added to the alloy.

8 Claims, No Drawings

DENTAL BRIDGE ALLOY

This invention relates to dental alloy suited for the production of fixed dental restorations such as crowns and bridges and is a continuation-in-part of my copending patent application Ser. No. 316,272 filed Dec. 18, 1972, now abandoned.

More particularly, this invention relates to a nickel-cobalt base dental alloy which is essentially free of molybdenum, tungsten, carbon and boron and has as its principal constituents cobalt, chromium and nickel, and contains small amounts of niobium or tantalum.

Although it has been stated in the past that alloys suitable for casting dentures are also suitable for casting fixed bridges and crowns, there are major differences in the mechanical properties required for these different applications.

At present, Type III gold alloys are universally used for fixed crown and bridge prosthesis since these are the only currently available alloys which possess the mechanical properties and have the melt-to-melt uniformity and appropriate crystal size and distribution for successful use in such dental applications.

An alloy for casting crowns and bridges must be burnishable which requires the low hardness associated with a low yield strength while one for casting dentures should be at least twice as strong and hence cannot be burnishable.

Burnishability may be defined as the ability of the metal to be worked in the mouth of a patient by small hand instruments, called burnishers, such that open margins of the alloy casting are closed and confirm precisely to the cavity margins in the tooth. The act of burnishing consists of indenting the alloy with a burnisher by hand force, bending the margin of the casting to close the open margin at the metal-tooth interface, and stretching and working the metal to match the contours of the tooth at the cavity margins. To be able to indent the cast crown with a hand instrument, the alloy must possess low hardness. To be able to bend the margin of the cast crown, the proportional limit of the metal alloy must be low enough so that it can be readily exceeded by the pressure of the hand and hence the alloy must possess low yield strength. To be able to manipulate the alloy and shape it to precisely match the contours of the natural tooth, the alloy must be malleable. The workability or malleability of the alloy is dependent not only on a low yield strength but also depends on high ductility. Hence, an alloy for crown and bridge castings should possess low hardness, low yield strength and high ductility.

For use in partial denture applications, an alloy must have high yield strength. Without high yield strength, the clasp components of a partial denture will deform during insertion or removal or under the masticatory loads encountered in use. A desirable denture alloy must have a yield strength of 70,000 – 80,000 psi while the most desirable crown and bridge alloy available is dental Type III gold alloys which have a yield strength of 27,000 – 34,000 psi. By virtue of the fact that the alloy possesses such low yield strength, its hardness is low enough to permit its indentation by manual pressure.

Also while in partial denture alloys, a maximum of 10 percent elongation is generally adequate to permit adjustment of the clasp components periodically, the ductility requirements of a crown and bridge alloy is much larger as exemplified by the fact that dental Type III gold alloys universally used for crown and bridge casting possesses a ductility of 22 – 27 percent elongation.

Efforts to introduce cobalt-nickel-chromium alloys for the processing of removable dentures was prompted by their high strength, corrosion resistance and low cost. These alloys were characterized by low ductilities until 1967 when Asgar's U.S. Pat. No. 3,544,315 introduced such an alloy possessing a ductility of up to 10 percent elongation. The level of ductility required for crowns or bridges, where not only bending but burnishing is necessary, has been lacking in the cobalt-nickel-chromium alloys available for dental uses. Crown and bridge applications require a ductility of at least 20 percent elongation.

It is a primary object of this invention to provide cobalt-nickel-chromium alloys which have properties equal to or exceeding those of Type III gold alloys currently used for the construction of dental crowns and bridges.

It is another primary object of this invention to provide alloys with mechanical properties not controlled by the conventionally known strengthening mechanisms of solid solution hardening or precipitation hardening but by controlling the crystal structure of the alloys through controlling the stacking fault energy of the alloy as well as the uniformity and fineness of the metal crystals.

Another object of this invention is the provision of such an alloy which possesses casting properties equal to or better than Type III gold alloys and can be fabricated by substantially the same current conventional dental procedures. Included in this object is the provision of such an alloy which is as ductile as Type III gold alloys currently used in crown and bridge applications.

A still further object of this invention is the provision of a cobalt-nickel-chromium alloy which possesses a yield strength of no more than 35,000 psi and a ductility of at least 20 percent elongation.

A further object of this invention is to provide a cobalt-nickel-chromium alloy wherein the ratio of cobalt to nickel and chromium is adjusted to be readily cast, free from blow holes and voids, into sheets as thin as 28 gauge and to which niobium and/or tantalum is added to stabilize its crystal structure in the desirable face centered cubic crystal lattic structure as well as to act as a nucleating agent for the crystals of the alloy base.

Other objects will be in part obvious and in part pointed out more in detail hereinafter.

The invention accordingly comprises the combination of elements disclosed herein and articles possessing the features, properties, and characteristics which are exemplified in the following disclosure.

When the element cobalt is heated above 500° C, its crystal structure is the ductile face centered cubic lattice (FCC). Upon cooling below 417° C, the crystal structure transforms to the less ductile hexagonal close packed structure (HCP). This is due to the formation of faults in the stacking of atoms below 417° C and hence cobalt is said to have low stacking fault energy (SFE), and undergoes allotropic transformation upon cooling. This allotropic transformation of cobalt is not desirable for crown and bridge alloys because it markedly reduces ductility. the SFE of cobalt can be raised, and hence its allotropic transformation is inhibited, by the addition of certain elements.

The addition of more than 26 percent nickel to cobalt in a binary cobalt-nickel alloy under equilibrium conditions, will inhibit the allotropic transformation and maintain the ductile FCC structure at room temperature. However, the addition of more than 65 percent nickel in the binary alloy system is harmful to the desirable properties of low proportional limit and high ductility because concentrations higher than 65 percent nickel causes the formation of the ordered superlattice $CoNi_3$ which raises the proportional limit and hardness and lowers the ductility.

Chromium, on the other hand, has the opposite effect of nickel on the SFE of a cobalt containing alloy, i.e., the addition of chromium lowers the SFE of cobalt resulting in the formation of more of the less ductile HCP structure at room temperature. However, the addition of chromium is essential because it imparts mandatory corrosion resistance to the alloy. When chromium is added, the minimum nickel content must be increased. Two atomic percent of nickel added to the alloy to counteract the adverse effect of one atomic percent of chromium on SFE. Since their atomic weights are almost equal, the addition of one percent of chronium, by weight, must, in the preferred embodiment of this invention, by offset by increasing the nickel content of an alloy by 2 percent, by weight, in order to maintain the same SFE in the alloy at room temperature.

Other corrosion inhibiting elements, such as molybdenum, have an adverse effect on the alloys of this invention due to an unfavorable effect on SFE and the formation of hardening precipitates that reduce ductility. Accordingly, a minimum of about 20 percent chromium by weight, should be used in the alloys.

As explained above, the effect of this amount of chromium on SFE must be balanced by the addition of 40 percent nickel, by weight, so that 60 percent of the alloy composition is consumed by this essential balance of chromium and nickel.

The remaining 40 percent of the alloy should, in the preferred embodiment, be balanced in its ratio of cobalt to nickel in accordance with the equilibrium conditions discussed above. Therefore, the minimum nickel content to produce an FCC binary cobalt-nickel alloy should preferably be 26 percent and the maximum should preferably be 65 percent. When the minimum nickel content necessary to maintain the FCC structure at room temperature is considered, the remaining 40 percent of a cobalt-nickel-chromium ternary alloy must be in the ratio of 26 percent nickel to 74 percent cobalt, or in the ratio of about 1 to 3. This would result in the incorporation of an additional 10 percent nickel and 30 percent cobalt to form the ternary alloys. the preferred ternary alloy composition which contains minimum nickel content to maintain the FCC structure at room temperature should, therefore, be 20 percent chromium, 50 percent nickel and 30 percent cobalt, by weight.

When maximum nickel content is considered on the other hand, the maximum nickel content in the remaining 40 percent to form the preferred ternary alloy could be as much as 65 percent or in the ratio of 65 percent nickel to 35 percent cobalt, or in the ratio of about 2 to 1. In the latter case, the ternary alloy that contains maximum nickel content and maintains the FCC structure at room temperature without the precipitation of $CoNi_3$ is 20 percent chromium, 67 percent nickel and 13 percent cobalt, by weight.

As indicated in the tables below, alloys 5 and 7 which possess the compositions indicated above are characterized by mechanical properties better than those of gold Type III alloys for crown and bridge applications especially when burnishability is considered. In fact, alloys 5, 6, 7 and 8, which according to the above considerations crystallize in the FCC structure, are of almost identical properties indicating that variations in nickel content from 50 – 67 percent and in cobalt content from 13 – 30 percent has no major influence on the mechanical properties so long as these ratios of these elements to each other as well as to chromium conform with the SFE considerations given above and the alloy is composed to crystallize in the desirable FCC structure.

An alloy for casting crowns and bridges should also possess good flowability in its molten state so that it can be cast into the continuous thin films which are necessary for the production of castings with the fine thin margins that are required by crown and bridge applications.

Thin castings are also necessary in producing what are termed veneer crowns where a cast crown which covers a prepared tooth is provided with an extremely thin cross-section on the facial surface to receive a porcelain or acrylic overlay for cosmetic purposes. To meet the standard test of flowability necessary for crown and bridge applications through the use of conventional dental procedures, an alloy must be capable of being consistently cast, free of blow holes and voids, into a sheet of metal 28 gauge thick, ⅜ inch wide and 1¾ inches long.

Currently available cobalt-nickel-chromium dental alloys having the highest flowability in the molten state, such as those disclosed by Asgar Pat. No. 3,544,315, Touceda Pat. No. 2,103,500, and Prosen Pat. No. 2,674,571 may not be cast into sheets as thin as 28 gauge due to their inadequate flowability in the molten condition. These alloys, which contain molybdenum to provide the strength properties required, do not meet the standard test for flowability required for crown and bridge applications.

It is evident from Table II below that the mechanical properties of alloys 5 – 8 vary over a wide range of up to 35 percent from one melt to another for the same composition. This variation is highly undesirable for commercial production and clinical manipulation and may be due to the fact that not only must an alloy have a high SFE, which was achieved through balancing the cobalt-nickel-chromium ratios in the alloy, but rapid crystallization of the liquid alloy is also necessary to maintain the desirable FCC structure. Raising SFE inhibits the transformation of the element cobalt to HCP upon cooling. However, the inherent tendency in the metal to transform continues to remain and tends to take place when the solidification is slow. In order for the ternary cobalt-nickel-chromium molten alloy to solidify, nuclei of crystallization first have to form. In the absence of additional elements, only a few nuclei are formed and the crystals begin to grow slowly to form a casting consisting of a few large crystals. Since the growth of these crystals is slow due to the small number of nucleation sites, cobalt will have the opportunity to transform. When the alloy possesses high SFE but slow rate of crystallization, cobalt transforms partially and the quantity transformed is not controlled and varies from melt-to-melt dependent upon many environmental factors surrounding the liquid metal and thus major variations in the mechanical properties occur from one melt to another. Accordingly, in order to completely inhibit the FCC to HCP transformation, not only is a high SFE necessary but a high rate of crystallization is also necessary.

A high rate of crystallization of the cobalt-nickel-chromium system can be achieved by the addition of nucleating agents. Any elements added to alloys meant for crown and bridge applications to provide nucleation sites, should be selected to also raise the SFE of the alloy. Further, they should possess an adequate solubility in, and a high melting point relative to, the base alloy to enable them to act as nucleating agents and should not deteriorate the mechanical properties of the alloy. Niobium and tantalum meet these requirements. As illustrated by examples 13 – 22, it was discovered that the addition of 2 percent tantalum or 1 percent niobium will accelerate the crystallization of the alloy through acting as nucleation sites due to their adequate solubility in the alloy and their high melting points of 2996° C and 2415° C, respectively. Niobium has a solubility of about 3 percent and tantalum of about 6 percent in the alloy. Alloys 13 – 22 are substantially of the same composition as alloys 4 – 8 except for their tantalum or niobium content. It is evident from Table II that the variations in the mechanical properties of alloys 13 – 22 were reduced to the acceptable 5 – 10 percent by the addition of niobium or tantalum to produce alloys of similar properties from one melt to another of the same composition.

When SFE considerations were not followed and cobalt-nickel-chromium ratios were reduced below the minimal nickel requirements as shown in examples 9 – 12, not only did the melt-to-melt variation in the mechanical properties reach almost 100 percent, but the property of ductility also deteriorated to below 20 percent and further to 5 percent elongation.

Although alloys 9, 10 and 11 should contain higher concentrations of the HCP phase, their mechanical properties make them suitable for crown and bridge applications. Naturally, such use is contingent upon controlling the chemistry of the alloys such that the variation from melt-to-melt for the same composition is reduced. The addition of 2 percent tantalum or 1 percent niobium to examples 9 – 11 reduced the extent of variation somewhat but not to the desired limits. However, the use of 4 percent tantalum or 2 percent niobium reduced the variation in the mechanical properties to within acceptable limits. In alloys 9 – 11 which have a high cobalt content, higher concentrations of tantalum and niobium were necessary because the alloys had lower SFE and larger quantities of tantalum or niobium were necessary to raise it.

Examples 23 – 28 are essentially alloys 9 – 11 after the addition of tantalum or niobium. Enough of the latter elements not only reduced variation from melt-to-melt, but also raised the yield strengths of the alloys and lowered their ductilities. The latter effect may be attributed to the fact that, at these concentrations, both niobium and tantalum rendered significant solid solution hardening of the alloy and/or caused the precipitation of small amounts of intermetallic compounds.

Niobium and tantalum have the effect of counteracting the harmful effect of chromium on the SFE of a cobalt containing alloy.

Specifically, one atomic percent of niobium counteracts the harmful effect of 2.5 atomic percent of chromium on the SFE. The atomic weight of chromium is roughly half that of niobium which means that the effect of one percent of niobium, by weight, counteracts the effect of 1.25 percent of chromium, by weight. On the other hand, the addition of more than about 2 percent of niobium causes the precipitation of intermetallic compounds and deteriorates ductility. The adverse effect on SFE of the 20 percent chromium required in a dental alloy, may be counteracted by the addition of both niobium and nickel. Since 2 percent niobium is a desirable maximum and counteracts the effect of 2.5 percent chromium, the effect of only 17½ percent chromium must be counteracted by nickel when 2 percent niobium is present. Since 2 percent nickel, by weight, counteracts the effect of 1 percent chromium, by weight, a minimum amount of 35 percent nickel, by weight, must be included in such a composition. Naturally, a decrease in the concentration of niobium must be accompanied by an increase in the concentration of nickel. For instance, decreasing the niobium content of the alloy by one percent must be accompanied by increasing nickel by 2.5 percent to maintain the same crystal structure and substantially the same properties in the final alloy. Tantalum can be substituted for niobium in about the ratio of 2 to 1, by weight, because it has an equivalent effect on SFE to that of niobium but twice the atomic weight. One percent of niobium is effective but a range of 1 to 3 percent can be used with the higher percentage of niobium being used for alloys with a low nickel-cobalt ratio.

In addition to the aforementioned essential elements, some other metallic and non-metallic elements may be present in the alloy, some as accidental impurities. Other elements are markedly detrimental to the mechanical properties required of crown and bridge applications and their presence in significant amounts cannot be tolerated.

Carbon, boron, gold, zirconium, manganese, copper, aluminum, titanium, tin and iron have varying degrees of favorable effect on the SFE of a cobalt containing alloy. Carbon and boron are highly effective in raising the SFE of the alloy. Nonetheless, the alloy must be essentially free of these elements (less than 0.02 percent carbon and 0.01 percent boron should be present) because their presence results in the formation of carbide and boride precipitates which are incoherent and embrittle the alloy.

Although gold has a favorable effect on the SFE of the alloy and may be present, it cannot be used in lieu of tantalum and niobium since its low melting point does not allow it to serve as a nucleating agent.

The solubility of zirconium in cobalt-nickel alloys is too limited for it to be effective in raising the SFE of the alloy. Manganese presents alloying difficulties and copper has a low melting point and does not act as a nucleating agent. Copper also lowers the corrosion resistance of the alloy. Aluminum has a low melting point and does not act as a nucleating agent and the presence of aluminum in nickel containing alloys results in the formation of $Ni_3Al$ intermetallic compounds which raises in strength and hardness of the alloy and lowers its ductility. Titanium acts in a similar fashion by causing the formation of $Ni_3Ti$. Tin may be incorporated in the alloy due to its favorable effect on SFE of the alloy as well as its ability to lower its melting point.

Iron which also a has a favorable effect on the SFE of a cobalt-containing alloy but its presence in significant amounts lowers the flowability and the corrosion resistance of the alloy and iron does not act as a nucleating agent.

Ruthenium, osmium, silicon, molybdenum, tungsten, iridium and platinum have unfavorable effects upon the SFE of cobalt containing alloys and encourage the formation of the less ductile HCP phase and should not be present in significant amounts. Less than 1 percent silicon and tungsten should be present and molybdenum should not be present in quantities of more than 2 percent. Sulphur content should not exceed 0.02 percent.

From the tables below, it is apparent that the basic alloy of this invention has properties which exceed those of Type III dental gold. Accordingly, the proportions of cobalt, nickel, and chromium in the alloy can be present outside the specific ratios indicated above and still obtain an alloy having mechanical properties essentially equivalent to Type III gold dental alloys. This is possible because some HCP crystal structure can be tolerated and yet the alloy will exhibit properties for a crown and bridge alloy of the same level as Type III dental gold alloys. Accordingly, an alloy which is essentially composed, by weight, of about 10 – 60 parts cobalt, 17 – 24 parts chromium, 20 – 75 parts nickel and up to 3 percent niobium or 6 percent tantalum made according to this invention will provide a dental alloy suited for crown and bridge applications. In the preferred alloy, 50 parts nickel, 30 parts cobalt, and 20 parts chromium form the alloy base to which is added 2 – 6 percent tantalum or 1 – 3 percent niobium. The presence of other elements can be tolerated only to the extent that they do not cause significant deterioration in the necessary mechanical properties of the alloy.

The chromium content should not be materially reduced or increased beyond the aforementioned ranges. An alloy having a low chromium content highly corrodes while excessive chromium content causes embrittlement. Increased cobalt content increases the quantity of the undesirable HCP structure, whereas increased nickel content increases the quantity of the desirable FCC structure in the alloy. The alloy of this invention, however, provides an excellent balance for crystal structure and mechanical properties.

The examples next set forth illustrate the properties of the alloy and the criticality of carbon and molybdenum. All alloys were made under a non-oxidizing atmosphere using induction type heating units to avoid carbon contamination. The alloys were cast by normal dental techniques in phosphate-bonded investments at 1600° F under a non-oxidizing atmosphere and quenched in cold water.

Table I describes compositions wherein the amounts of critical elements especially molybdenum and carbon in Examples 1 and 2 are outside the essential ranges claimed. The physical properties of these alloys summarized in Table II are the ranges of four specimens made from each composition. The values of the yield strength and ductility show that alloys 1 and 2 fail to meet the essential criteria for alloys for crown and bridge applications in one or more respects, i.e., low elongation, and/or undesirable hardness by virtue of high yield strength.

Example 3 is Type III gold alloy having the currently acceptable properties required for crown and bridge applications.

Examples 4 – 8 are alloys prepared such that their cobalt-nickel-chromium ratios are balanced to produce an alloy of high SFE that crystallizes in the FCC structure.

Examples 9 – 12 are alloys prepared such that their cobalt-nickel-chromium ratios are not desirable since their ratios encourage the alloy to crystallize in the less ductile HCP structure.

Examples 13 – 22 are of the same compositions as alloys 4 – 8 but contained tantalum or niobium as an additional element to further raise the alloys SFE as well as to act as a nucleating agent.

Examples 23 – 28 are of the composition as alloys 9 – 12 but contained tantalum or niobium to raise the alloys SFE and decrease the concentration of the HCP phase as well as to act as a nucleating agent. Although these alloys possess mechanical properties that make them suitable for use in lieu of Type IV dental gold alloy for long span bridges which require a higher yield strength of 37,000 to 49,000 and a ductility of 4 percent or more, the alloys are not suitable for the processing of crowns or regular bridges.

Examples 29 – 32 represent the extreme concentrations of the cobalt-nickel-chromium alloys to which the extreme concentration of tantalum or niobium is added. These alloys may be used for long span bridges but not for crowns or regular bridges.

TABLE I

| ALLOY COMPOSITIONS - WEIGHT PERCENT | | | | | | | | |
|---|---|---|---|---|---|---|---|---|
| Example | Ni | Co | Cr | Nb | Ta | Mo | C | OTHERS |
| 1 | 14.2 | 52 | 26.1 | — | — | 4 | 0.22 | Fe 1.2, Si 0.58, Mn 0.7 |
| 2 | 2.7 | 61.53 | 27.66 | — | — | 4.27 | 0.22 | Fe 1.27, Si 0.57, Mn 0.66, W 1.05 |
| 3 | GOLD TYPE III ALLOY | | | | | | | |
| 4 | 70 | 10 | 20 | | | | | |
| 5 | 67 | 13 | 20 | | | | | |
| 6 | 60 | 20 | 20 | | | | | |
| 7 | 50 | 30 | 20 | | | | | |
| 8 | 45 | 35 | 20 | | | | | |
| 9 | 40 | 40 | 20 | | | | | |
| 10 | 30 | 50 | 20 | | | | | |
| 11 | 20 | 60 | 20 | | | | | |
| 12 | 10 | 70 | 20 | | | | | |
| 13 | 69.3 | 9.9 | 19.8 | 1 | — | — | | |
| 14 | 68.6 | 9.8 | 19.6 | — | 2 | — | | |
| 15 | 66.3 | 12.9 | 19.8 | 1 | — | — | | |
| 16 | 65.7 | 12.7 | 19.6 | — | 2 | — | | |
| 17 | 59.4 | 19.8 | 19.8 | 1 | — | — | | |
| 18 | 58.8 | 19.6 | 19.6 | — | 2 | — | | |
| 19 | 49.5 | 29.7 | 19.8 | 1 | — | — | | |
| 20 | 49.0 | 29.4 | 19.6 | — | 2 | — | | |
| 21 | 44.5 | 34.6 | 19.8 | 1 | — | — | | |
| 22 | 44.1 | 34.3 | 19.6 | — | 2 | — | | |
| 23 | 39.2 | 39.2 | 19.6 | 2 | — | | | |
| 24 | 38.4 | 38.4 | 19.2 | — | 4 | | | |

TABLE I-continued

| ALLOY COMPOSITIONS - WEIGHT PERCENT | | | | | | | | |
|---|---|---|---|---|---|---|---|---|
| Example | Ni | Co | Cr | Nb | Ta | Mo | C | OTHERS |
| 25 | 29.4 | 49 | 19.6 | 2 | — | | | |
| 26 | 28.8 | 48 | 19.2 | — | 4 | | | |
| 27 | 19.6 | 58.8 | 19.6 | 2 | — | | | |
| 28 | 19.2 | 57.6 | 19.2 | — | 4 | | | |
| 29 | 48.5 | 29.1 | 19.4 | 3 | — | | | |
| 30 | 47.0 | 28.3 | 18.7 | — | 6 | | | |
| 31 | 65.0 | 12.6 | 19.4 | 3 | — | | | |
| 32 | 63.0 | 12.2 | 18.8 | — | 6 | | | |

TABLE II

| MECHANICAL PROPERTIES | | | | |
|---|---|---|---|---|
| Example | Yield Strength × 10³ psi | Ductility Percent | UTS × 10³ psi | Maximum Castibility Gauge |
| 1 | 60.0 | 10 | 97.5 | 24 |
| 2 | 70.0 | 5.5 | 85.0 | 24 |
| 3 | 32.0 | 23 | 56.0 | 28 |
| 4 | 28.2 - 35.4 | 20 - 29 | 57 - 64.1 | 24 |
| 5 | 23 - 28.7 | 27 - 35.7 | 51 - 59.4 | 24 |
| 6 | 22.1 - 28.2 | 28 - 37.8 | 50 - 58.5 | 24 |
| 7 | 22.4 - 29.1 | 28.7 - 36.7 | 51 - 57.9 | 24 |
| 8 | 26.2 - 34.9 | 22.9 - 34.5 | 48 - 57.1 | 24 |
| 9 | 25.1 - 37.8 | 19 - 29.9 | 49.1 - 54.9 | 24 |
| 10 | 23.4 - 30.9 | 19 - 39.6 | 47 - 56.2 | 24 |
| 11 | 22 - 31.3 | 14 - 23.5 | 46 - 57.9 | 24 |
| 12 | 18.3 - 30.1 | 4.9 - 10.1 | 40 - 51.1 | 24 |
| 13 | 31 - 33.3 | 26 - 27.6 | 59.1 - 61.9 | 28 |
| 14 | 29 - 30.5 | 28 - 29 | 59 - 60.5 | 28 |
| 15 | 27.9 - 29 | 30 - 32 | 57 - 58.9 | 28 |
| 16 | 28.3 - 31.1 | 31 - 32.7 | 58 - 59.4 | 28 |
| 17 | 27 - 29.2 | 32 - 34.1 | 57.1 - 59.5 | 28 |
| 18 | 27.7 - 29.3 | 33 - 35.2 | 57.4 - 59.7 | 28 |
| 19 | 25 - 27.3 | 33 - 36.3 | 52.5 - 54.9 | 28 |
| 20 | 25 - 26 | 34 - 37.1 | 51 - 53.2 | 28 |
| 21 | 28.9 - 32.7 | 23.1 - 25.3 | 48.7 - 51.1 | 28 |
| 22 | 30.1 - 31.6 | 25.2 - 27.1 | 49.2 - 51.4 | 28 |
| 23 | 38.3 - 42.3 | 17 - 18.5 | 60 - 61 | 28 |
| 24 | 36 - 37.1 | 25 - 27.2 | 61.4 - 64 | 28 |
| 25 | 39.7 - 42.3 | 17.1 - 19.3 | 62 - 64.5 | 28 |
| 26 | 41.3 - 43.7 | 18.2 - 18.9 | 61.5 - 63.4 | 28 |
| 27 | 46.8 - 49.6 | 12.9 - 14.1 | 68.7 - 71.1 | 28 |
| 28 | 45.7 - 47.6 | 14 - 16.3 | 69.1 - 74.7 | 28 |
| 29 | 46.0 - 48.3 | 19 - 20.3 | 69.6 - 73.4 | 28 |
| 30 | 42.1 - 44.2 | 19 - 20.7 | 69.4 - 72.4 | 28 |
| 31 | 41.0 - 43.3 | 15.2 - 16.2 | 63.2 - 67.6 | 28 |
| 32 | 42.0 - 46.6 | 22.5 - 24.8 | 67.2 - 69.9 | 28 |

As will be apparent to persons skilled in the art, various modifications of the above described invention will become readily apparent without departure from the spirit and scope of the invention.

I claim:

1. A highly ductile cobalt-chromium-nickel dental alloy having a ductility of about 20 percent or more elongation, a yield strength of about 35,000 or less and low work hardening characteristics suited for crown and bridge applications requiring deformation by hand burnishing in the mouth of a patient, said alloy having no more than 0.02 percent carbon and being essentially free of boron, molybdenum, titanium, aluminum and tungsten to prevent the formation of hardening precipitates thereof in the alloy and having an alloy base consisting essentially of, by weight, about 10 to 60 percent cobalt, 17 to 24 percent chromium, and 20 to 75 percent nickel as the essential major alloying elements, and an element of the group consisting of tantalum and niobium alloyed therewith to promote a high rate of crystallization and provide uniformity and fineness of crystal size, said alloying element being present in an amount of up to about 4 percent tantalum or an equivalent atomic weight of niobium.

2. An alloy according to claim 1 wherein nickel is present, by weight, in the alloy base in an amount about twice the amount of chromium plus an additional amount in the ratio to cobalt of between about 1 to 3 and 2 to 1.

3. An alloy according to claim 2 wherein the alloying element is present in the amount of 2 percent tantalum or the equivalent atomic weight of niobium.

4. A dental casting made of the alloy of claim 1.

5. An alloy according to claim 2 wherein the alloy base consists essentially of about 20 percent chromium, 50 to 67 percent nickel, and 13 to 30 percent cobalt, by weight, and the alloying element is present in the amount of up to about 2 percent tantalum or the equivalent atomic weight of niobium.

6. A dental casting made of the alloy of claim 5.

7. A dental casting made of the alloy of claim 4.

8. The method of making a cobalt-nickel-chromium alloy suited for use as a gold alloy substitute for dental crown and bridge applications requiring hand burnishing in the mouth of a patient and having a controlled high stacking fault energy, a ductility of about 20 percent or more elongation, a yield strength of about 35,000 psi or less, and low work hardening characteristics, said alloy having an alloy base consisting essentially of about 20 to 75 percent nickel, 17 to 24 percent chromium, and 10 to 60 percent cobalt, by weight, comprising the steps of providing nickel in an amount of about twice as much as the chronium present, of providing the remainder of the alloy base by adding cobalt and an additional amount of nickel in the ratio of nickel to cobalt of between about 1:3 and 2:1, by weight and the step of stabilizing the uniformity and fineness of the crystal structure of the alloy by adding an element selected from the group consisting of niobium and tantalum in an amount of up to about 4 percent tantalum, by weight, or the equivalent atomic weight of niobium to promote a high rate of crystallization and provide fineness and uniformity of grain size in the alloy.

* * * * *